US00PP27488P3

(12) United States Plant Patent
O'Connell

(10) Patent No.: US PP27,488 P3
(45) Date of Patent: Dec. 20, 2016

(54) ***AEONIUM* PLANT NAMED 'FIESTA'**

(50) Latin Name: ***Aeonium* hybrid**
Varietal Denomination: Fiesta

(71) Applicant: Renee O'Connell, Escondido, CA (US)

(72) Inventor: Renee O'Connell, Escondido, CA (US)

(73) Assignee: Altman Plants, Vista, CA (US)

( * ) Notice: Subject to any disclaimer, the term of this patent is extended or adjusted under 35 U.S.C. 154(b) by 75 days.

(21) Appl. No.: 14/544,911

(22) Filed: Mar. 6, 2015

(65) Prior Publication Data

US 2016/0270283 P1 Sep. 15, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen Redden

(57) ABSTRACT

A new and distinct *Aeonium* cultivar named 'Fiesta' is disclosed, characterized by a unique, stable, quadricolor variegation, displaying leaves of muted forest green, splashed with lime green, with rose red & burgundy blushing of the outer leaves of the rosette in high light environments, as well as during cooler winter temperatures. Additionally, the new cultivar 'Fiesta' is more easily and more rapidly propagated due to moderately fast, robust growth, enhancing production times. The new cultivar 'Fiesta' offsets freely at an early age, quickly forming attractive clumps, enhancing propagation intervals. The new variety is an *Aeonium*, part of the Crassulaceae complex that includes *Aeonium, Echeveria, Pachyphytum, Graptopetalum, Sedum* and others. *Aeonium* is a popular genus, typically produced as container plants for the patio or for use as landscape plants.

2 Drawing Sheets

Figure 1:
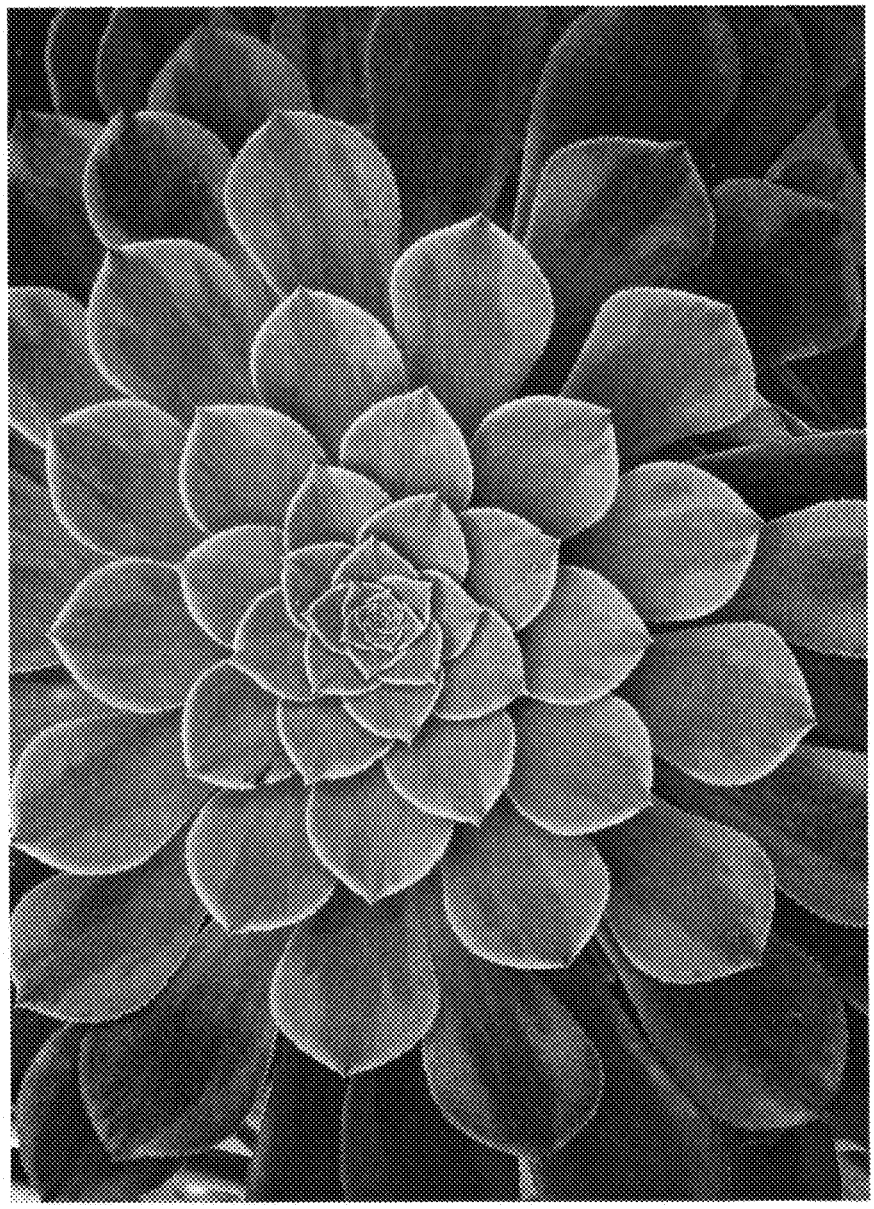

Latin name of the genus and species: *Aeonium* hybrid.
Variety denomination: 'FIESTA'.

BACKGROUND OF THE INVENTION

The new cultivar, *Aeonium* 'Fiesta', was found by the inventor, Renee O'Connell, as a naturally occurring, branch, mutation in an existing population of the unpatented unnamed, *Aeonium* cultivar referred to as *Aeonium* '#13'. The parent variety is the product product of a planned breeding program in a commercial greenhouse in Vista, Calif. conducted by inventor, Renee O'Connell. *Aeonium* 'Fiesta' was discovered by the inventor, Renee O Connell, in April of 2011, in a block of motherstock of *Aeonium* '#13' at a commercial greenhouse in Vista. Calif.

Asexual reproduction of the new cultivar 'Fiesta' was first performed in Vista, Calif., at a commercial greenhouse, by vegetative cuttings in May of 2011. 'Fiesta' has since produced multiple generations and has shown that the unique features of this cultivar are stable and reproduced true to type.

SUMMARY OF THE INVENTION

The cultivar 'FIESTA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FIESTA' These characteristics in combination distinguish 'FIESTA' as a new and distinct *Aeonium* cultivar:

1. Displays a unique, stable, quadricolor variegation, displaying leaves of muted forest green, splashed with lime green, with rose red & burgundy blushing of the outer leaves of the rosette in high light environments, as well as during cooler winter temperatures.
2. Offsets freely and forms attractive clusters at an earlier age than many other comparable *Aeonium* varieties.
3. Easily and rapidly propagated due to its robust growth; faster and easier to propagate than many other comparable *Aeonium* cultivars.
4. Freely offsetting, enhancing propagation and production.

Plants of the new cultivar 'FIESTA' are similar to plants of the parent, *Aeonium* '#13' in most horticultural characteristics, however, plants of the new cultivar 'FIESTA' differs in the following;

1. Exhibits a unique, quadricolor variegation, displaying leaves of muted forest green splashed with lime green, with rose red and burgundy blushing of the outer leaves of the rosette in highlight environments, as well as during cooler winter temperatures, not exhibited by the *Aeonium* hybrid #13.
2. Exhibits a more compact morphology than the *Aeonium* hybrid '#13'.
3. More uniform arrangement of the leaves.

COMMERCIAL COMPARISON

Plants of the new cultivar 'FIESTA' are comparable to the unpatented, commercial variety *Aeonium arboreum* 'Tricolor'. The two *Aeonium* varieties are similar in most horticultural characteristics; however, the new variety 'FIESTA' differs in the following:

1. Displays a unique, quadricolor variegation, displaying leaves of muted forest green splashed with lime green, with rose red and burgundy blushing of the outer leaves of the rosette in high light environments, as well as during cooler winter temperatures. 'Tricolor' has an overall different variegation pattern, and does not develop the deep burgundy blushing to the outer foliage.
2. Freely produce offsets, producing an attractive, low-growing cluster, whereas *Aeonium arboreum* 'Tricolor' is a solitary plant until it attains a much taller height, and therefore cannot produce the same low growing, attractive cluster
3. By virtue of freely producing offsets, shortens the propagation and production interval, as compared with *Aeonium arboreum* 'Tricolor'.

Plants of the new cultivar 'FIESTA' can also be comparable to the unpatented commercial variety *Aeonium* 'Sunburst'. The two *Aeonium* varieties are similar in most horticultural characteristics; however, the new variety 'FIESTA' differs in the following:

1. Different variegation pattern, and 'Sunburst' does not develop the burgundy coloration to outer leaves.
2. Exhibits early, profuse offsetting, not exhibited by *Aeonium* 'Sunburst'.
3. Displays a more compact morphology than does *Aeonium* 'Sunburst'.
4. By virtue of freely producing offsets, shortens propagation and production intervals, as compared to *Aeonium* 'Sunburst'.

BRIEF DESCRIPTION OF THE PHOTOGRAPHS

The accompanying photograph in FIG. 1 illustrates in full color the winter coloration of the new plant *Aeonium* 'Fiesta' as grown in a commercial greenhouse in Vista, Calif.

Figure 2:
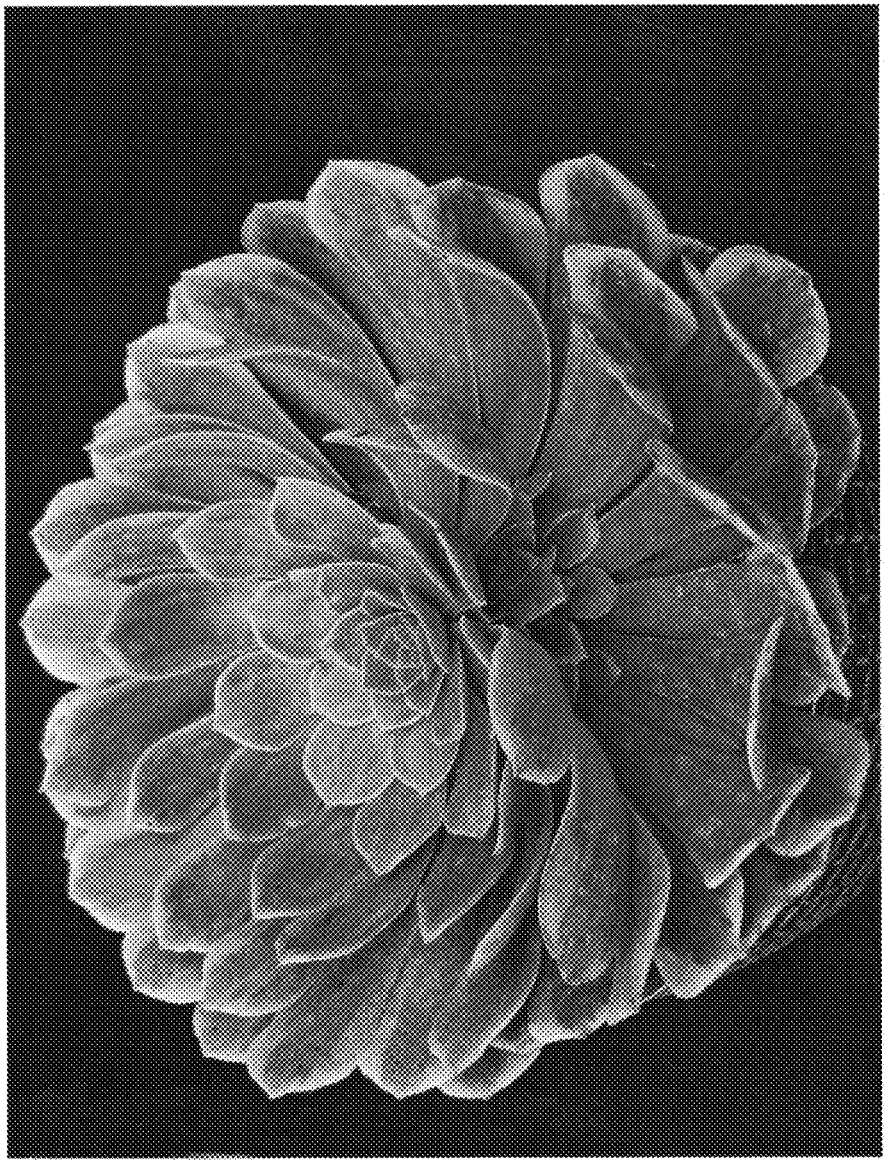

FIG. 2 illustrates in full color the emergence of the offsets from between leaves of the rosette of *Aeonium* 'Fiesta' as grown in a commercial greenhouse in Vista. Plants illustrated in FIG. 2 have been grown in a shaded greenhouse, and the variegation is not well expressed. Age of the plants photographed is approximately 14 weeks from a rooted sideshoot plantlet.

The photographs were taken using conventional techniques and although colors may appear different from actual colors due to light reflectance it is as accurate as possible by conventional photographic techniques. All photographs provided by the breeder.

DETAILED BOTANICAL DESCRIPTION

In the following description, color references are made to the Pantone Process Color System Guide, Pantone CYMK, 2014, except where general terms of ordinary dictionary significance are used. The following observations and measurements describe 'Fiesta' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Aeonium* hybrid 'FIESTA'.

PROPAGATION

Type of propagation typically used: Terminal vegetative divisions.

Time to initiate roots: About 19 days at approximately 23° C.

Root description: Fibrous.

PLANT

Age of plant described: Approximately 4 months.

Container size of the plant described: 16 cm.

Growth habit: Upright, caulescent, with a terminal rosette, freely offsetting from below rosette and between leaves of the rosette to produce cluster.

Height: Approximately 10.7 cm to top of highest leaf. Height in cm to top of inflorescence is unknown as plant has been undergoing propagation, and has not yet flowered.

Plant spread: 20.5 cm.

Growth rate: Moderately fast.

Branching characteristics: Freely offsetting.

FOLIAGE

Leaf:

*Arrangement.*—Rosulate.

*Average length.*—Approximately 8.5 cm.

*Longest length.*—Approximately 10.5 cm.

*Widest width.*—Approximately 3.1 cm.

*Width at base.*—0.9 cm.

*Shape of blade.*—Oblanceolate.

*Apex.*—Acuminate.

*Base.*—Cuneate.

*Margin.*—Ciliate.

*Texture of top surface.*—Glabrous.

*Texture of bottom surface.*—Glabrous.

*Quantity of leaves per plant.*—Approximately 95.

*Color.*—Young foliage upper side, margin: Near P 160-6 U Pantone. Young foliage, upper side, lighter green: Near P 159-5 U Pantone. Young foliage upper side, darker green: Near P 159-8 U Pantone. Young foliage, under side: Near P 159-8 U Pantone. Young foliage underside, towards stem: Near P 164-5 U Pantone. Mature foliage upper side, margin: Near P 160-6 U Pantone. Mature foliage upper side, lighter green: Near P 164-13 U Pantone. Mature foliage, upper side, darker green: Near P 159-15 U Pantone. Mature foliage under side, closer to apex: Near P 59-15 U Pantone. Mature foliage, under side, near stem: Near P 164-2 U Pantone. Mature foliage, under side, margin: Near P 160-13 U Pantone. Mature foliage, upper side, winter color, near apex: Near P 74-14 U Pantone. Mature foliage, upper side, winter color, other areas: Near P 74-4 U Pantone and P 74-16 U Pantone. Mature foliage, upper side, winter color, green area: Near P 159-13 U Pantone. Mature foliage, upper side, winter color, marginal cilia: Near P 7-9 U Pantone.

*Venation.*—There is no visual appearance of venation. Indistinguishable from leaf blade.

FLOWER

Natural flowering season: Unknown, plant has not flowered to date.

REPRODUCTIVE ORGANS

Unknown, plant has not flowered to date.

OTHER CHARACTERISTICS

Fruits and seeds: Unknown, plant has not flowered to date.

Temperature tolerance: Tolerates temperatures from approximately −2 C to 32 C.

Disease/pest resistance: Displays the same disease and pest resistance of any other comparable *Aeonium*.

Drought tolerance: Tolerates at least 3 weeks of high temperatures without supplemental water, showing no serious damage to plant.

What is claimed is:

1. A new and distinct cultivar of *Aeonium* plant named 'FIESTA' as herein illustrated and described.

* * * * *